(12) United States Patent
Kvam et al.

(10) Patent No.: US 10,000,742 B2
(45) Date of Patent: Jun. 19, 2018

(54) DEVICE AND METHOD OF COLLECTION FOR RNA VIRUSES

(71) Applicant: GENERAL ELECTRIC COMPANY, Schenectady, NY (US)

(72) Inventors: Erik Leeming Kvam, Niskayuna, NY (US); Robert Scott Duthie, Schenectady, NY (US); John Richard Nelson, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 88 days.

(21) Appl. No.: 14/945,483

(22) Filed: Nov. 19, 2015

(65) Prior Publication Data

US 2017/0145387 A1    May 25, 2017

(51) Int. Cl.
| | |
|---|---|
| *C12N 7/00* | (2006.01) |
| *B01L 3/00* | (2006.01) |
| *C12N 15/10* | (2006.01) |
| *C12Q 1/68* | (2018.01) |
| *C12Q 1/70* | (2006.01) |

(52) U.S. Cl.
CPC ............... *C12N 7/00* (2013.01); *B01L 3/508* (2013.01); *C12N 15/1017* (2013.01); *C12Q 1/6806* (2013.01); *C12Q 1/70* (2013.01); *C12Q 1/701* (2013.01); *B01L 2200/082* (2013.01); *C12N 2760/14111* (2013.01); *C12N 2760/14151* (2013.01); *C12N 2760/14163* (2013.01)

(58) Field of Classification Search
None
See application file for complete search history.

(56) References Cited

U.S. PATENT DOCUMENTS

| | | | |
|---|---|---|---|
| 5,985,327 A * | 11/1999 | Burgoyne | .......... C12N 15/1017 424/484 |
| 8,685,748 B2 | 4/2014 | Lloyd et al. | |
| 8,877,060 B2 | 11/2014 | Sehgal | |
| 9,040,675 B2 | 5/2015 | Bales et al. | |
| 9,040,679 B2 | 5/2015 | Kvam et al. | |
| 9,044,738 B2 | 6/2015 | Li et al. | |
| 2005/0208501 A1 | 9/2005 | Goldrick | |
| 2012/0189711 A1 | 7/2012 | Greenberg et al. | |
| 2012/0202190 A1 | 8/2012 | Ching et al. | |
| 2013/0157283 A1 | 6/2013 | Yung et al. | |
| 2013/0289257 A1 | 10/2013 | Bales et al. | |
| 2013/0338351 A1 * | 12/2013 | Kvam | ...................... B01J 20/24 536/25.42 |

FOREIGN PATENT DOCUMENTS

| | | |
|---|---|---|
| WO | 1994020216 A1 | 9/1994 |
| WO | 2011/113043 A2 | 9/2011 |
| WO | 2014025787 A1 | 2/2014 |
| WO | 2014/072354 A1 | 5/2014 |

OTHER PUBLICATIONS

Keeler et al., Avian Diseases, 2012, 56:200-207.*
Kvam et al., "Device for Separation and Collection of Plasma", U.S. Appl. No. 14/712,290, filed May 14, 2015.
Abdelwhab, E. M. et al., "The use of FTA filter papers for diagnosis of avian influenza virus," Journal of Virological Methods, vol. 174, pp. 1-4 (2011).
GE Life Sciences, "FTA Sample Collection Cards and Kits," Retrieved from the Internet URL: http://www.gelifesciences.com/webapp/wcs/stores/servletcatalog/en/GELifeSciences-nl/products/AlternativeProductStructure_17098/, on Feb. 7, 2017, pp. 1.
GE Healthcare Life Sciences, Whatman (TM) FTA Elute (TM) Retrieved from the Internet URL: https://www.gelifesciences.com/gehcls_images/GELS/Related%20Content/Files/1390468964833/litdoc28984402_20161015133858.pdf, on May 25, 2017, pp. 1-4.
Meyer, E.P., "Use of filter paper (FTA (R)) technology for sampling, recovery and molecular characterisation of rabies viruses," Journal of Virological Methods, vol. 140, pp. 174-182 (2007).
Li, Y., et al., "An optimized method for elution of enteroviral RNA from a cellulose-based substrate," Journal of Virological Methods, vol. 186, pp. 62-67 (2012).
International Search Report and Written Opinion issued in connection with corresponding PCT Application No. PCT/EP2016/077384 dated Feb. 21, 2017.

* cited by examiner

*Primary Examiner* — Stacy B Chen

(57) ABSTRACT

The present disclosure generally relates to a method and device for inactivation and dry storage, under ambient conditions, of a biological sample containing RNA virus. Methods for collecting and recovering RNA from a biological sample and subsequent analysis for a virus are also provided.

24 Claims, 9 Drawing Sheets

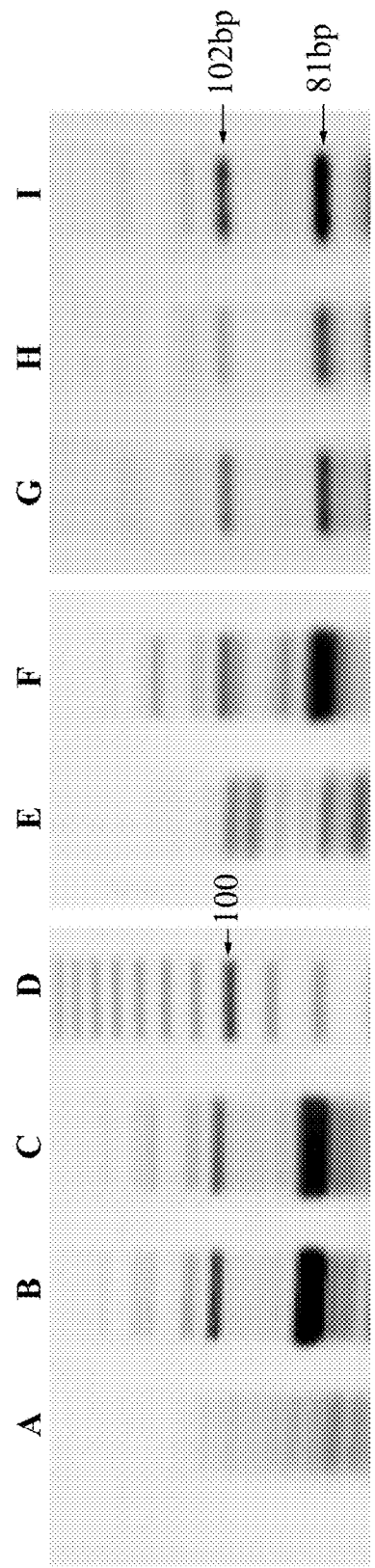

DEVICE AND METHOD OF COLLECTION FOR RNA VIRUSES

SEQUENCE LISTING

The instant application contains a Sequence Listing which has been submitted electronically in ASCII format and is hereby incorporated by reference in its entirety. Said ASCII copy, created on Nov. 17, 2015, is named 283554-1_SL.txt and is 1,602 bytes in size.

BACKGROUND

RNA viruses, and more specifically their nucleic acids, are one of the most difficult biomolecules to stabilize because of both chemical self-hydrolysis and enzyme-mediated degradation. The temperature of sample storage is often a key determinant for the quality of the RNA virus sample and, therefore, samples containing RNA viruses are typically maintained and shipped in refrigerated states (i.e., 4° C. or less). Further, handling of virus containing samples is precarious due to risk of viral infections, if the sample cannot be rendered inactive.

Accordingly, current methodologies for preserving nucleic acids, such as RNA, under ambient conditions in a liquid state have focused on deactivation of RNases through the use of, for example, detergents, chaotropic compounds, reducing agents, transitional metals, organic solvents, chelating agents, proteases, RNase peptide inhibitors, and anti-RNase antibodies. Additional efforts have focused on modifying RNA chemically in order to prevent trans-esterification and self-hydrolysis.

Most commercially available RNA preservation products can only preserve RNA in a liquid state for days or weeks at room temperature. Technologies that claim successful collection and preservation of RNA in a dry format typically require that the RNA is first "pre-purified" and concentrated from the biological material (e.g., biological samples such as blood, serum, tissue, saliva, etc.) prior to storage of the RNA.

Accordingly, methods and devices that integrate nucleic acid extraction, stabilization, and storage/preservation from a biological sample within a single process are desirable and needed. Further, for safe handling, biological inactivation of the virus is also desirable. Such method and devices would permit long-term storage of nucleic acid under ambient conditions and allow the intact nucleic acid to be rapidly tested or recovered for further analysis without the burdensome handling requirements associated with an infectious substance.

BRIEF DESCRIPTION

The present disclosure generally relates to methods and devices that integrate the steps of nucleic acid extraction and stabilization from a biological specimen collected on a dry solid matrix, thereby enabling preservation and storage of RNA viruses wherein the virus is rendered inactivated. The RNA quality of the collected sample is maintained during the steps of collection, extraction, stabilization, and storage and/or shipping.

In some embodiments, RNA stored in an ambient state on dry solid matrices may be subjected to a process to release the RNA from the solid matrix in an intact format that is suitable for further analyses. Methods for determining the presence or absence of RNA virus within the sample are described. Methods of using the solid matrices of the invention for extracting and storing nucleic acids from a biological sample are also provided.

In some embodiments, the RNA is viral RNA present for example in a blood sample.

BRIEF DESCRIPTION OF DRAWINGS

These and other features, aspects, and advantages of the chemically modified porous membranes will become better understood when the following detailed description is read with reference to the accompanying drawings in which like characters represent like parts throughout the drawings.

FIG. 2A is the top view and FIG. 2B is the bottom view.

FIGS. 9A-C are images of electrophoresis gels showing extraction-free isothermal amplification and detection of Ebola RNA directly from dried blood spots on filter paper to demonstrate combined isothermal reverse transcription/amplification from RSM. FIG. 9A columns A through C are control reactions; column D additionally contained 0.5 µl of whole human blood. FIG. 9B columns E and F are control reactions where E did not contain template while F contained Zaire Ebolavirus RNA. FIG. 9C, columns G and H are reaction volumes of washed RSM that had previously been spotted with human blood and Ebola RNA, column H had extra copies of Zaire Ebolavirus, and column I is unwashed 1 RSM that was spotted with human blood and Ebola RNA.

DETAILED DESCRIPTION

An RNA virus is a virus that comprises ribonucleic acid (RNA) in its genetic material. Certain RNA viruses called retroviruses may further convert RNA genetic material into DNA during the virus life cycle. Several RNA viruses are known to elicit serious diseases including Ebola hemorrhagic fever, influenza, hepatitis, and West Nile fever. Notable retroviruses implicated in disease include HIV. Viral hemorrhagic fevers (VHFs) refer to a group of illnesses caused by several distinct families of viruses. In general terms, VHFs are used to describe one of a number of infectious diseases that interfere with the blood's ability to clot. The viruses that cause VHF belong to four families of hemorrhagic viruses: the arenaviruses, filoviruses, bunyaviruses, and flaviviruses. The arenaviruses include the Lassa fever virus and Machupo, Junin, Guanarito, and Sabia hemorrhagic fever viruses. Among the filoviruses are the notorious Ebola virus and Marburg virus. The bunyaviruses include Rift Valley fever (RVF), Crimean-Congo hemorrhagic fever (CCHF), and hantaviruses. The viruses of yellow fever and dengue are flaviviruses.

VHFs are all RNA viruses that are covered, or enveloped, in a fatty (lipid) coating. The ability of these viruses to survive depends on an animal or insect host organism or a host-derived fluid. Humans are infected when they encounter infected hosts. However, with some of these viruses, after the transmission from the natural host, there can be person-to-person transmission through host-derived fluids. Human cases or outbreaks of hemorrhagic fevers caused by these viruses occur sporadically and irregularly. The occurrence of outbreaks cannot be easily predicted. Further, with a few exceptions, there are no effective drug treatments for VHFs and, thus, outbreaks of VHFs are viewed as significant public health risks.

VHFs have an infectious dose of 1-10 organisms and thus highly contagious. Early detection and isolation is key to controlling outbreaks. Generally, for VHFs, such as Ebola virus, the virus can be detected in blood only after the onset of symptoms, usually fever. A diagnostic test, such as real-time PCR testing is recommended, however facilities that perform viral testing are often far-removed and thus specific collection, handling, and shipping protocols are implemented for potentially infectious samples.

Figure 1:
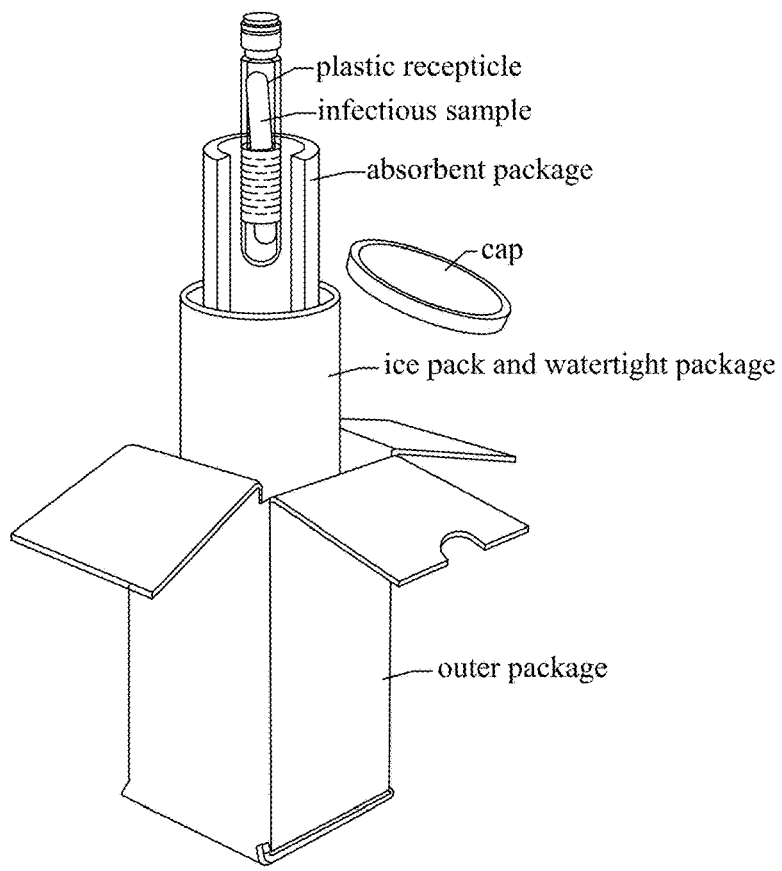
FIG. 1 provides an illustration of Center for Disease Control (CDC) guidelines for field collection and shipment of Ebola specimens (prior art).
Figure 1:
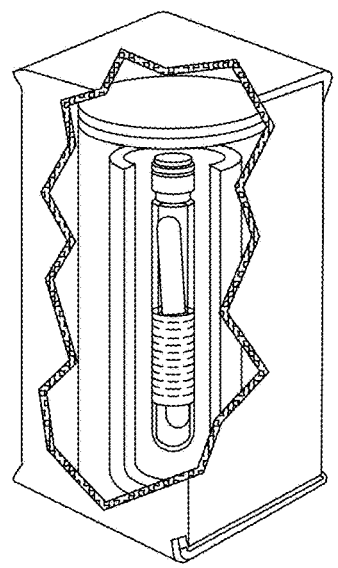

The Center for Disease Control (CDC) guidelines for collection and shipment are shown in FIG. 1 for Ebola specimens, and are representative of the current state of the art. Normally per CDC guidelines, a minimum collection volume of 4 mL of whole blood is preferred, and sample shipment at 2-8° C. is recommended. As a Category A infectious substance, a triple packaging system that consists of a primary sealable container wrapped with absorbent material, a secondary container (watertight, and leak-proof), and an outer shipping package are used. This triple packaging system ensures that the live and potentially infectious biological liquids are contained during sample transport.

Additional CDC guidelines exist for testing infectious samples. Sample processing methods are generally performed under bio-safety level 3 (BSL-3) conditions to reduce viral infectiousness and permit processing of the live samples that are received from the field. After performing a viral inactivation step, BSL-2 conditions are permitted to continue sample testing. For molecular diagnosis of any pathogen, the inactivation process should ensure a total loss of the infectiousness while conserving the integrity of the nuclei acids for proper identification of the virus.

In certain embodiments, a device for collection and storage of a biological sample for subsequent diagnostic analysis of RNA viruses is provided. The device comprises a treated dry solid matrix for holding the collected biological sample, a frame for holding the solid matrix, and a storage sleeve for encasing the frame and dry solid matrix after collection of the sample. In certain embodiments, the treated dry solid matrix allows for ambient extraction and storage of nucleic acids (e.g., RNA, DNA, or a combination thereof) from the sample wherein the presence of RNA virus can be determined by analysis for viral RNA. In a further embodiment, the device comprises a frame for holding a filtration membrane and a treated dry solid matrix for the purposes of fractionating the collected biological sample at the point-of-collection.

The term "extraction" refers to any method for separating or isolating the nucleic acids from a sample, more particularly from a biological sample. Nucleic acids such as RNA and DNA may be released, for example, by cell-lysis. In one embodiment, nucleic acids may be released during evaporative cell-lysis. In another embodiment, the cells are lysed upon contact with the matrix comprising cell lysis reagents. Contacting a biological sample comprising cells to the matrix results in cell lysis which releases nucleic acids, for example by using FTA™ Elute cellulose papers. To be clear, methods for extracting, collecting, preserving, and recovering nucleic acids from the dry solid substrates are described. Extraction as used herein may refer to either extraction of the nucleic acid from the cell (e.g. cell lysis) or recovery from the matrix after storage ("matrix extraction"). Methods for extraction-free rapid testing from the dry solid substrates are also described wherein the collected nucleic acid does not have to be extracted from the matrix prior to analysis.

In one embodiment, RNA in the biological sample maybe released onto the dry solid matrix by evaporative sample cell lysis during sample drying, or by the presence of compounds impregnated within the chemically modified solid matrix that, upon contact with the biological sample, results in cell lysis and the release of nucleic acids (e.g., FTA™ and FTA™ Elute cellulose papers). In this manner, the extraction of nucleic acids, particularly RNA, and more specifically viral RNA, from a sample (e.g., an unpurified biological sample) is such that the nucleic acids may be maintained on the treated solid matrix in a non-pure state and analyzed. The terms "storage" or "preservation" may be used interchangeably herein with respect to maintaining the extracted nucleic acids in a format suitable for further analysis and diagnosis.

The term "nucleic acid" refers to all forms of RNA (e.g., mRNA, miRNA, rRNA, tRNA, piRNA, ncRNA), DNA (e.g., genomic DNA, mtDNA), as well as recombinant RNA and DNA molecules or analogues of DNA or RNA generated using nucleotide analogues. The nucleic acid molecules can be single stranded or double stranded. Strands can include the coding or non-coding strand. Fragments of nucleic acids of naturally occurring RNA or DNA molecules are encompassed by the present invention and may be recovered using the compositions and methods disclosed. "Fragment" refers to a portion of the nucleic acid (e.g., RNA or DNA). In certain embodiments, the targeted nucleic acid is RNA of the virus.

In certain embodiments, the dry solid matrix includes, but is not limited to, cellulose-based products, cellulose, cellulose acetate, glass fibers, or any combination thereof. A solid matrix of the present application may be porous. In particular embodiments, the solid matrix is a porous cellulose paper from Whatman™, such as 903, 31-ETF, FTA™ or FTA™ Elute (GE HealthCare Life Sciences, Buckinghamshire, UK). The terms membrane, paper, cellulose paper, solid matrix, and substrate may be used interchangeably throughout this disclosure.

In certain embodiments, the dry solid matrix is treated with a protein denaturant, a reducing agent, a buffer, and optionally a free-radical trap or RNase inhibitor, which are incorporated into the solid matrix in a dry state. In other embodiments, the treated dry solid matrix is of the type described in U.S. Pat. No. 9,040,679, issued May 26, 2015, incorporated herein in its entirety. In one preferred embodiment, the treated dry solid matrix is of the type described in U.S. Pat. No. 9,044,738 issued Jun. 2, 2015 and in U.S. Pat. No. 9,040,675 issued May 26, 2015, both of which are herein incorporate in their entirety.

One of skill in the art will appreciate that many such methods exist to accomplish incorporation of the composition into the dry solid matrix to provide a treated matrix. The methods include, but are not limited to dipping, spray coating, or a wet batch process. Following incorporation of the composition into the dry solid matrix, the resulting treated solid matrix may be dried in accordance with any appropriate method.

As defined herein, a "biological sample" includes but is not limited to blood, serum, tissue, nasal mucous, and saliva obtained from any organism, including a human, or fluids derived from cultured cells. Biological samples may be obtained by an individual undergoing a self-diagnostic test (e.g., blood glucose monitoring) or by a trained medical professional through a variety of techniques including, for example, aspirating blood using a needle or scraping or swabbing a particular area, such as a lesion on a patient's skin. Methods for collecting various biological samples are well known in the art. In certain embodiments, the biological sample refers to a sample for diagnostic purposes of identifying the presence of RNA viruses. In certain embodiments, the RNA virus is Ebola.

In certain embodiments, the composition of the treated solid matrix comprising a protein denaturant, a reducing agent, and a buffer is present in the dry solid matrix of this disclosure, which may be re-hydrated with a biological sample during sample collection and extraction steps. The composition may comprise one or more of each of the above-listed components. The composition may optionally further comprises an ultraviolet (UV) inhibitor, a free-radical trap, an RNase inhibitor, a chelator, or any combination thereof. The skilled artisan will appreciate that numerous protein denaturants are known in the art and can be empirically selected for use in the compositions and methods described here.

Exemplary protein denaturants include, but are not limited to, guanidinium thiocyanate, guanidinium hydrochloride, arginine, sodium dodecyl sulfate (SDS), urea, or any combination thereof.

Without intending to be limited to a particular protein denaturant, one schematic of an exemplary protein denaturant is set forth below:

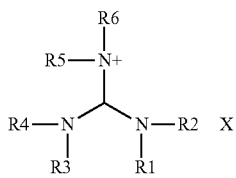

wherein each R may be independently a member selected from the group consisting of hydrogen, a heteroatom containing radical or a hydrocarbon radical.

The heteroatom containing radical is a group comprising a member or members selected from nitrogen, oxygen, sulfur, phosphorus, silicon, and boron. It is an object to bind a guanidine-containing compound using reactive functional groups. Typical reactive groups, which bear heteroatoms, include epoxy, acrylate, maleimide, acyl halide, alkyl halide, azide, cyanate ester, isocyanate, aryl halide, aldehyde, amine, oxime, thiol, alcohol, acid, aziridine, azo, Isothiocyanate, anhydride, mixed anhydride, lactone, sultone, and ketone.

The hydrocarbon radical is a group comprising both carbon and hydrogen, though may also contain heteroatoms to enhance hydrophilicity. It is an object to bind a guanidine-containing compound using reactive functional groups. Typical reactive groups, which bear hydrocarbon, include allyl, styryl, vinyl, and alkyne. Heteroatom containing hydrocarbon groups include 2, 3 or 4-oxystyryl, aminoallyl, oxyallyl, oxyvinyl, amino vinyl. X is an anion, which is a radical containing one or more formal negative charge(s). A member or members selected from the group consisting of chloride, thiocyanate, sulfate, phosphate, bromide, chlorite, chlorate, thiosulfate, carbonate, hydrogen carbonate, acetate, formate, hydrogen phosphate, dihydrogen phosphate. It is envisioned that one or more anions may be used in and combinations of anions bearing various levels (divalent, monovalent, trivalent) of formal charge may be used. The molecular weight of the anion may vary from 10 to 100,000.

In certain embodiments, the protein denaturant is a metal thiocyanate salt comprising a Group 1 or Group 2 metal cation. The metal thiocyanate salt includes but is not limited to sodium thiocyanate, potassium thiocyanate, magnesium thiocyanate, calcium thiocyanate, barium thiocyanate, and zinc thiocyanate.

The term "reducing agent" refers to a chemical species that provides electrons to another chemical species. A variety of reducing agents are known in the art, and the exemplary list provided below and in the claims is in no way intended to limit the reducing agent(s) that could be used in the compositions and methods of the present disclosure. Exemplary reducing agents include dithiothreitol (DTT), 2-mercaptoethanol (2-ME), and tris(2-carboxyethyl)phosphine (TCEP) and their related salts (e.g., TCEP-hydrochloride). Moreover, any combination of these or other reducing agents may be used to practice the invention. In particular embodiments, the reducing agent is TCEP. In particular, embodiments, the TCEP can be added as its hydrochloride salt, TCEP-HCl.

Buffer as used herein includes, for example, 2-Amino-2-hydroxymethyl-propane-1,3-diol (Tris), 2-(N-morpholino)ethanesulfonic acid (MES), 3-(N-morpholino)propanesulfonic acid (MOPS), citrate buffers, 4-(2-hydroxyethyl)-1-piperazineethanesulfonic acid (HEPES), and phosphate buffers. This list of potential buffers is for illustrative purposes only. The skilled artisan would recognize that the pH of the buffer selected for use in the compositions and methods disclosed herein is relevant. The pH of the buffer will typically be in the range of 3 to 8.

As indicated above, the composition present in the treated solid matrix may optionally comprise a UV protectant or a free-radical trap. In certain aspects of the invention, a UV protectant or a free-radical is required in the composition of the incorporated in the dry solid matrix for the extraction and storage of nucleic acids. Without intending to be limited to any specific UV protectant, exemplary agents include, for example, hydroquinone monomethyl ether (MEHQ), hydroquinone (HQ), toluhydroquinone (THQ), and ascorbic acid or vitamin C. In certain aspects, the free-radical trap is MEHQ or THQ. The terms "UV protectant" or "free radical trap" may be used interchangeably herein with respect to maintaining the extracted nucleic acids in an unmodified state for further analysis. The composition in the solid matrix may also include RNase inhibitors such as vanadyl ribonucleoside complex (VRC) or any of the commercially available RNase inhibitors (e.g., SUPERase-In™, Thermo Fisher Scientific, Waltham, Mass.).

In certain embodiments, the matrix further comprises an RNase inhibitor, wherein the RNase inhibitor comprises vanadyl ribonucleoside complex (VRC), a nucleotide analogue, or a commercially available RNase inhibitor (e.g., SUPERase-In™). The RNase inhibitor may further comprise pyrophosphate compounds. In one embodiment, sodium pyrophosphate dibasic may be used as an RNase-inhibitor. One or more embodiments of the RNase inhibitor may further comprise triphosphate salts, such as sodium triphosphate. In one example, addition of sodium pyrophosphate to acid-titrated buffer enhances RNA stability in both liquid state and dry-formats.

Embodiments of the matrix comprise acid or acid-titrated buffer reagents in a dry-state, which may be re-hydrated during extraction of nucleic acids from the biological sample. Examples of the acid include, but are not limited to, acetic acid, citric acid, tartaric acid, phosphoric acid, hydrochloric acid, Tris(2-carboxyethyl) phosphine-hydrochloric acid (TCEP-HCl), oxidized Tris(2-carboxyethyl) phosphine-hydrochloric acid (TCEP-O-HCl), sulfuric acid, nitric acid, vanillic acid, 3-(N-morpholino)propanesulfonic acid, or combinations thereof. As noted, the matrix provides an acidic pH on hydration, which extracts and stabilizes the extracted nucleic acids, wherein the hydration may be achieved by adding a sample, water or any other solution (e.g., a buffer solution). One or more embodiments of the matrix provide a pH in a range from 2 to 7 on hydration. In some embodiments, the matrix provides a pH in a range from 3 to 6 on hydration.

The device comprises a frame for holding the treated solid matrix. In certain embodiments, the frame may be rigid capable of supporting the treated solid matrix. The frame may have an alignment mechanism and offsets for inserting the matrix into the frame. In certain embodiments, the frame may have four side rails extending connected such to form corners in a rectangle type shape. At least one of the side rails having an edge portion which is sized and positioned suitably to receive the solid matrix.

In other embodiments, the frame is one as described in U.S. patent application Ser. No. 14/712,290 filed Apr. 6, 2015 and incorporated herein in its entirety. In certain embodiments, the frame is a one piece substrate having an outer flexure and an inner flexure. The flexures are configured to hold the treated dry solid matrix as well as a second collection membrane or matrix which was capable of collecting the biological sample and transferring a portion of the sample to the treated dry solid matrix. As such, in certain embodiments the biological sample, for example a blood spot, may be added directly to the treated dry solid matrix. In an alternative method, the biological sample may be collected on a separate matrix and transferred to the treated dry solid matrix. The treated dry solid matrix thus acting as a separation membrane and the terms may be used interchangeably. The inner flexure is formed from a plurality of first slots and the outer flexure is formed from a plurality of second slots. The inner flexure is configured to align a distal end of the separation membrane (treated solid matrix) under a distal end portion of the outer flexure. The outer and inner flexures are further configured to align a proximal end of the collection membrane under the distal end portion of the outer flexure and a distal end portion of the inner flexure such that the proximal end of the collection membrane has a defined overlapping contact area with the distal end of the separation membrane. The overlapping contact area between the two membranes within the substrate facilitates proper separation and collection of plasma from the blood samples. As such the device maybe used to extract or elute key components of the sample, more specifically RNA, for further testing.

Figure 2A:
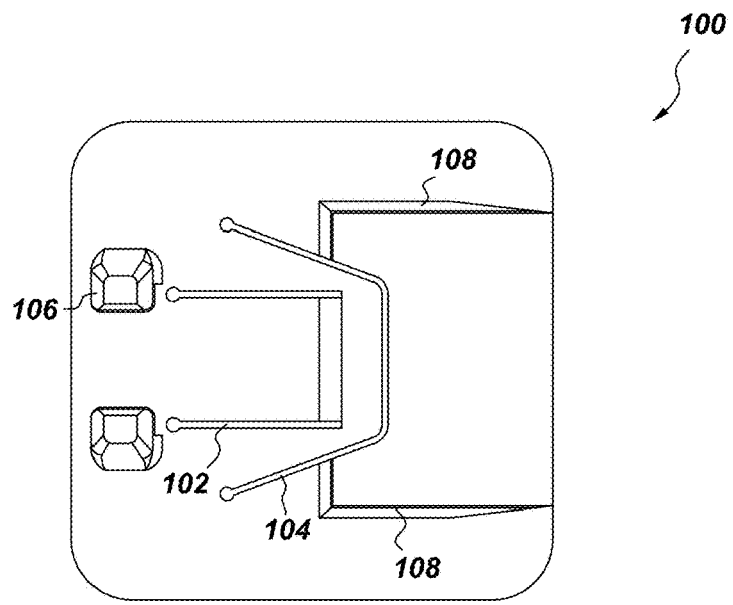
FIGS. 2A-B provides an illustrated example of one type of frame for the dry solid matrix.
Figure 2B:
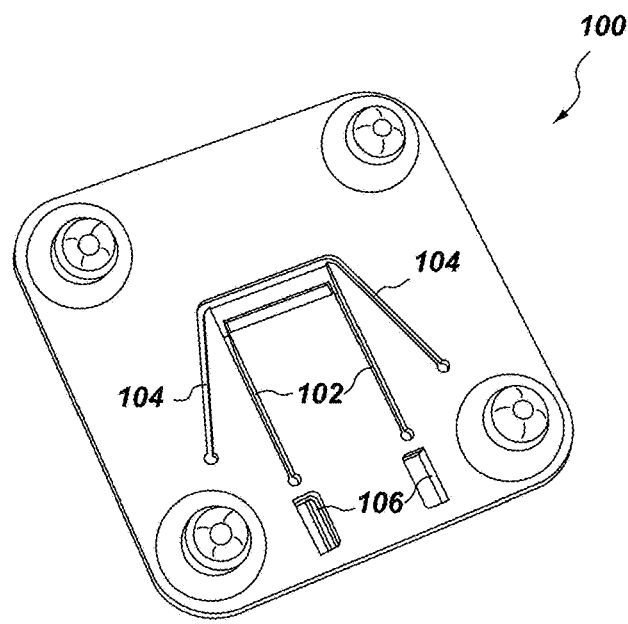
Figure 3:
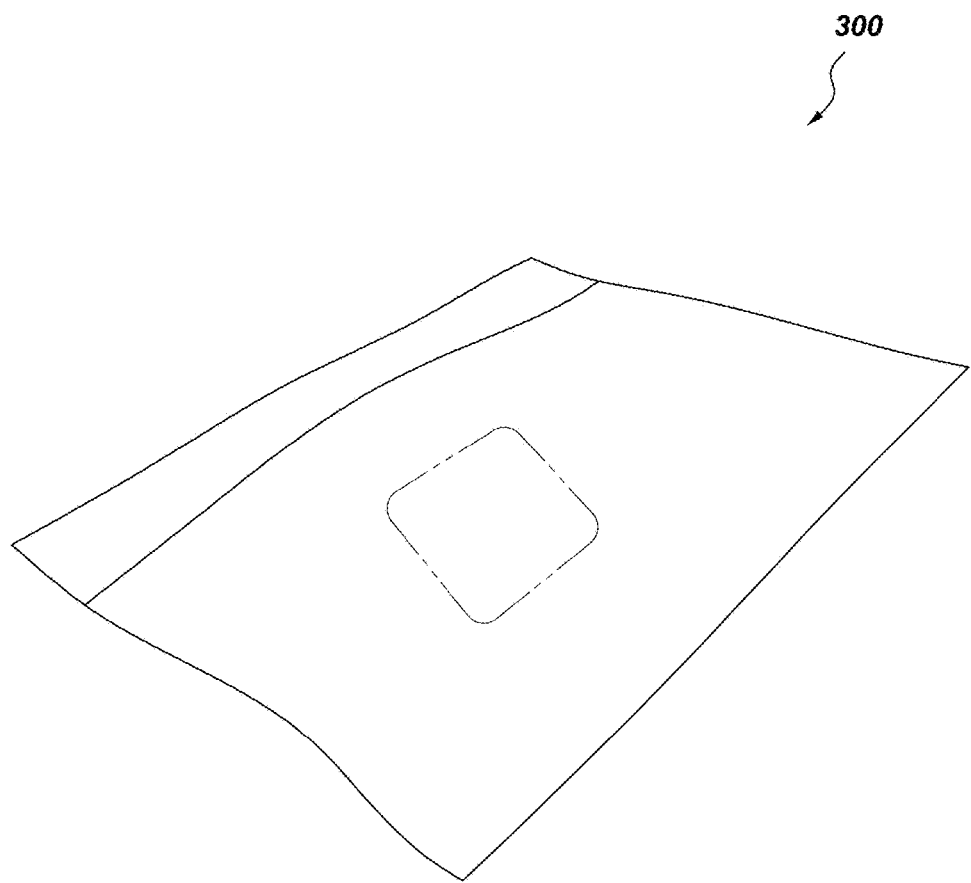
FIG. 3 is an illustration of a storage sleeve for encasing the dry solid matrix and frame.

FIG. 2A and FIG. 2B are representative views of one embodiment of the invention of the frame configured as the plasma clip 100. FIG. 2A shows the clip, 100, which includes an inner flexure 102 and an outer flexure 104. The clip 100 further includes a plurality of holding mechanism 106, a plurality of guiding mechanism 108, and a plurality of fixtures 110 which are shown in FIG. 2B.

In certain embodiments, the frame may be a polymer material such as polypropylene, nylon (polyamide), high density polyethylene (HDPE), and polyetheretherketone (PEEK). In certain other embodiments, the frame may have different shape such as circular, oval, rectangle, and the like.

The device may comprise a storage sleeve. In certain embodiment, the storage sleeve may be configured to allow transport and safe handling of the biological sample contained on the solid substrate from one location to another. It also may allow for archival storage of the collected sample for later analysis. In certain embodiments the storage sleeve may have a pocket for receiving the frame containing the treated solid matrix and one or more tabs connected with the sleeve that can be positioned in a manner to provide complete enclosure of the frame and matrix within the sleeve. In some embodiments, the storage sleeve may be configured in various shapes, sizes, and/or colors for easy identification. In certain embodiments sample identification may be performed by marking the sleeve, in other embodiments, marking may be done by using an identification tag attached to the device, such as an RFID chip or a barcode. A tracking system utilizing such storage sleeves can allow for rapid identification of archival biological samples such that the location of the sample in transit or in testing can be readily identified by physical connection with the corresponding storage sleeve.

Methods of using the device described herein are further provided. In one embodiment, the method allows for storage and/or preservation of RNA viruses in a dry state wherein the virus is inactivated. In another embodiment the method further provides for integrate nucleic acid extraction and stabilization from a biological sample, whereby the extracted nucleic acid, more specifically viral RNA, is tested for the diagnosis of an RNA virus. In a further embodiment, the method enables characterization of the RNA virus and/or the host transcriptome.

The method further comprises prolonged storing of RNA in an intact form under a dry format and ambient conditions, and wherein any virus present in the biological sample is rendered inactive. In certain embodiment, the method comprises storing the extracted nucleic acids on the matrix in a dry state at ambient temperature for a period of days to weeks. In some embodiments, the nucleic acids may be stored for more than a one-month period. In some embodiments, the nucleic acids may be stored for more than a six months period. As RNA is generally prone to degradation, the extraction and preservation of RNA using the matrix is useful and may further be used for various downstream applications.

Figure 4:
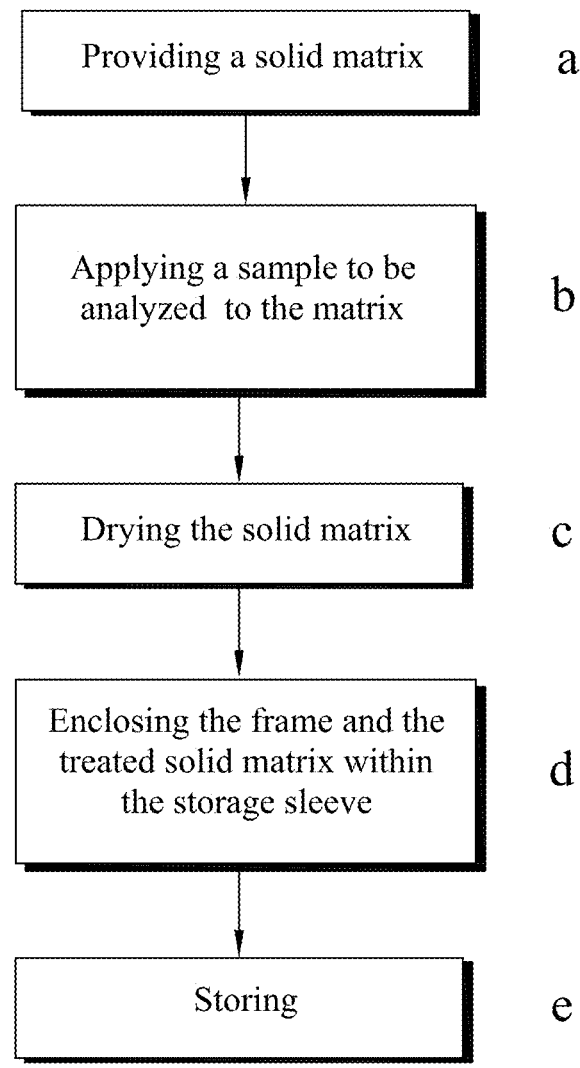
FIG. 4 is a flow chart outlining a method for inactivation and dry storage of a biological sample containing RNA virus.

In certain embodiments, as shown in the flow chart of FIG. 4, the method comprises the steps of: a) providing a solid matrix, wherein a composition comprising at least one protein denaturant, at least one reducing agent, a biological buffer, and optionally a free-radical trap or RNase inhibitor is incorporated into the solid matrix in a dried format; b) applying a sample to be analyzed for an RNA virus (e.g., a biological sample) onto the treated solid matrix of the device to extract the nucleic acids, wherein the matrix is contained by the frame of the device; c) drying the solid matrix; d)

enclosing solid matrix within the storage sleeve. In certain embodiments, the solid matrix is held within a frame for ease of handling.

In certain embodiments the methods further comprise at least one of storing the device (FIG. 4, step e), containing the nucleic acids on the solid matrix in a dry state under ambient conditions. The device may then be transported to a remote location for testing under ambient conditions. As such, while the virus is inactive, the RNA is preserved in an intact state to allow for proper analysis.

In certain embodiment, step d and step e, as shown in FIG. 4 may be reversed in that the sample may be dried after sealing in the storage sleeve. For example, a desiccant maybe added to the sleeve to effect drying or to complete the drying of the sample.

In certain aspects, the solid matrix is a porous cellulose-based paper such as the commercially available 903, 31-ETF, or FTA Elute™. Performance of this method permits the storage of nucleic acids, particularly RNA which is widely known to be an unstable biomolecule to store, in a dry format (e.g., on a solid matrix) under ambient temperatures. The samples utilized in this method include but are not limited to biological samples such as blood, serum, tissue, nasal mucous, and saliva obtained from any organism, including a human, or fluids derived from cultured cells.

The method delineated above may optionally include a step to recover the nucleic acids from the solid matrix for further analysis.

As such, in a further aspect of the invention a method is included for further processing of the sample after the storage as described above in FIG. 4. The method comprises the additional steps of extracting the nucleic acid from the stored sample or applying a workflow to analyze the sample directly from the matrix.

In certain embodiments, the solid matrix comprises a fixed composition of dry reagents, which enables efficient extraction of nucleic acids, from the biological sample, such as RNA, upon hydration, followed by stabilization of the extracted RNA at ambient temperature. As such, in certain embodiments the matrix maintains the stability and integrity of RNA at a desired level subsequent to extraction from a biological sample. In one embodiment, the matrix is impregnated with nucleic acid stabilizing reagents. These stabilizing reagents may include RNase inhibitors, acid-titrated buffer, or chelating agents (e.g. EDTA). The composition may further comprise an ultraviolet (UV) inhibitor or a free-radical scavenger.

In certain embodiments therefore, RNA may be recovered by rehydrating the solid matrix (e.g., cellulose paper) in an aqueous solution, a buffer solution, as defined above, or an organic solution. After extraction from the matrix, the recovered RNA may be analyzed for diagnostic purposes such as determining viral origin. More specifically, the RNA is associated with an RNA virus.

Alternatively, the RNA may be recovered from the solid matrix by electroelution. One of skill in the art will appreciate that any method capable of recovering RNA from the solid matrix may be used to practice the disclosed methods.

As such, in certain embodiment, the RNA extraction matrix is a solid phase extraction matrix. A matrix, where the solid phase extraction method is used, is referred to herein as a solid phase extraction matrix. Solid-phase extraction (SPE) technology may be leveraged to reduce the extraction times of high purity nucleic acids for sequencing and other applications. The solid phase extraction is an extraction method that uses a solid phase and a liquid phase to isolate one or more molecules of the same type, or different types, from a material. The solid phase extraction matrix is used, for example, to purify a sample upstream of a chromatographic or other analytical method. One example of the method comprises loading a sample (e.g., a biological sample) onto the solid phase extraction matrix, storing the matrix at ambient temperature to achieve a substantially dry state, and rehydrating the matrix with a suitable buffer to differentially extract RNA from the matrix.

In a further aspect of the invention, a method is included for further processing of the sample after the storage as described above in FIG. 4. The method comprises the additional steps of extracting the nucleic acid from the matrix. As such the purified nucleic acid can be further processed or analyzed. Alternatively, the nucleic acid can be processed or analyzed directly from the matrix. In this embodiment, the matrix containing the nucleic acid may be added directly to the workflow. In certain embodiments, the sample may be analyzed or processed without further purification of the nucleic acid fraction.

In certain aspects of the method, the solid matrix is a porous cellulose-based paper such as the commercially available 903, 31-ETF, or FTA Elute™. Performance of this method permits the storage of nucleic acids, particularly RNA which is widely known to be an unstable biomolecule to store, in a dry format (e.g., on a solid matrix) under ambient temperatures. The samples utilized in this method include but are not limited to biological samples such as blood, serum, tissue, nasal mucus, and saliva obtained from any organism, including a human.

In certain aspects of the method, the solid matrix may be analyzed without a separate extraction step or RNA recovery step. For example, a portion of the solid matrix containing a dried biological sample may be added directly to an enzymatic reaction for detection purposes. A suitable enzymatic reaction includes a reverse transcription reaction. In a further embodiment, the reverse transcription reaction may be coupled with a DNA amplification reaction, such as PCR or qPCR. In yet a further embodiment, the DNA amplification reaction is an isothermal reaction using an isothermal DNA polymerase. In one embodiment, the solid matrix is a porous cellulose paper from Whatman™, such as FTA™ Elute (GE HealthCare Life Sciences, Buckinghamshire, UK). In some embodiments, the non-eluted solid matrix may be analyzed as recited in Publication number WO2014072354 A1 published on May 15, 2014.

EXAMPLES

The following examples are offered by way of illustration and not by way of limitation.

Example 1

Inactivation and Detection of Ebola Virus

Vero cells were obtained from ATCC and were routinely passaged in T-75 flasks using standard tissue culture techniques based on the specifications provided by the supplier. On the day preceding the assays, the cells were split 1:2 to assure they were in an exponential growth phase at the time of infection. Total cell number and percent viability determinations were performed using a hemacytometer and trypan blue exclusion. Cell viability must be greater than 95% for the cells to be utilized in the assay.

The virus used for this assay was Zaire ebolavirus strain 199510621. For each assay, a pre-titered aliquot of virus was removed from the freezer (−80 C) and allowed to thaw slowly to room temperature in a biological safety cabinet in a BSL-4 laboratory. The virus was diluted in tissue culture medium or whole mouse blood to achieve the inoculum required for experiments.

In order to determine if filter paper eluate is directly cytopathic to Vero cells, 1 or 2-7 mm punches from each filter paper (T, R, E) were added to 1 mL of cell culture medium. Composition of the filter paper is shown in Table 1 below.

After 30 minutes at room temperature the samples were vortexed at high speed for 1 minute and a dilution series (1:10, 1:50, 1:100) was made in untreated cell culture medium. 1 mL of the undiluted or diluted eluates were then added to a confluent monolayer of Vero cells in a T-25 flask in duplicate. After one hour at 37° C., 4 mL of additional untreated cell culture medium was added to the flasks and they were monitored for 7 days. Any apparent cyptopathic effects (CPE) were recorded using a standardized scale (0 to 4+ CPE). A summary of the cytopathic effects from filter paper eluate is provided in Table 1 below.

TABLE 1

Summary of cytopathic effect of tested filter papers.

| Filter Paper Grade | Composition | CPE Observed | | | |
|---|---|---|---|---|---|
| | | Undiluted eluate | 1:10 dilution | 1:50 dilution | 1:100 dilution |
| T | 31-ETF (untreated cellulose) | No | No | No | No |
| R | RSM (TCEP-HCl, GuSCN, MOPS, THQ) | Yes | No | No | No |
| E | FTA Elute (non-buffered GuSCN) | Yes | No | No | No |

In order to determine if the filter papers inactivate live EBOV, cell-culture derived virus ($1.7 \times 10^5$ and $1 \times 10^3$ PFU/25 μL) was added to duplicate samples of each paper and allowed to dry at room temperature. Cell culture medium containing no virus was included as a negative control. A positive control containing 10 PFU of virus was used to infect a monolayer of cells (not spotted on filter paper) to demonstrate that if a small amount of virus is present then our method will ensure efficient EBOV propagation and detection. After drying, a 7 mm punch was added to 1 mL cell culture medium followed by incubation for 30 minutes at room temperature and vigorous mixing to ensure release of any active virus particles into the cell culture eluate. A 1:10 dilution of this primary eluate was then transferred to a confluent monolayer of Vero cells. After a 1 hour infection step, additional cell culture medium was added to the flask and the cells were observed for 7 days for cytopathic effects (CPE). On day 7 post-infection, the supernatant from each flask was collected and transferred to a new confluent monolayer of Vero cells and this flask was observed for 7 additional days for CPE. After this second incubation (14 days total), the supernatant from each flask was collected and analyzed by plaque assay and western blot for EBOV antigen. A summary of the results of the viral inactivation study are provided below in Table 2.

TABLE 2

Evidence of EBOV inactivation on filter paper

| | CPE in Flask 1 (Days 1-7) | CPE in Flask 2 (Days 8-14) | Average PFU/mL in Flask 1 and 2 Supernatant |
|---|---|---|---|
| 10 PFU EBOV positive control | Yes | Yes | $1.4 \times 10^6$ |
| Filter R; 0 PFU | No | No | 0 |
| Filter R; $1 \times 10^3$ PFU | No | No | 0 |
| Filter R; $1.7 \times 10^5$ PFU | No | No | 0 |
| Filter E; 0 PFU | No | No | 0 |
| Filter E; $1 \times 10^3$ PFU | No | No | 0 |
| Filter E; $1.7 \times 10^5$ PFU | No | No | 0 |
| Filter T; 0 PFU | No | No | 0 |
| Filter T; $1 \times 10^3$ PFU | No | No | 0 |
| Filter T; $1.7 \times 10^5$ PFU | Yes | Yes | $1.9 \times 10^5$ |

The results in Table 2 show a noticeable loss of virus on untreated cellulose (T) during drying and recovery, but complete inactivation of EBOV is noted on treated cellulose (R, E). Because Ebola peak titers approach $\sim 10^6$ in infected individuals, the observed inactivation of $\sim 10^5$ infectious particles on RSM (R) and FTA Elute (E) is clinically significant. RSM refers to RNA stabilization matrix, which is one embodiment of the matrix as described in aforementioned U.S. Pat. No. 9,044,738.

Figure 5:
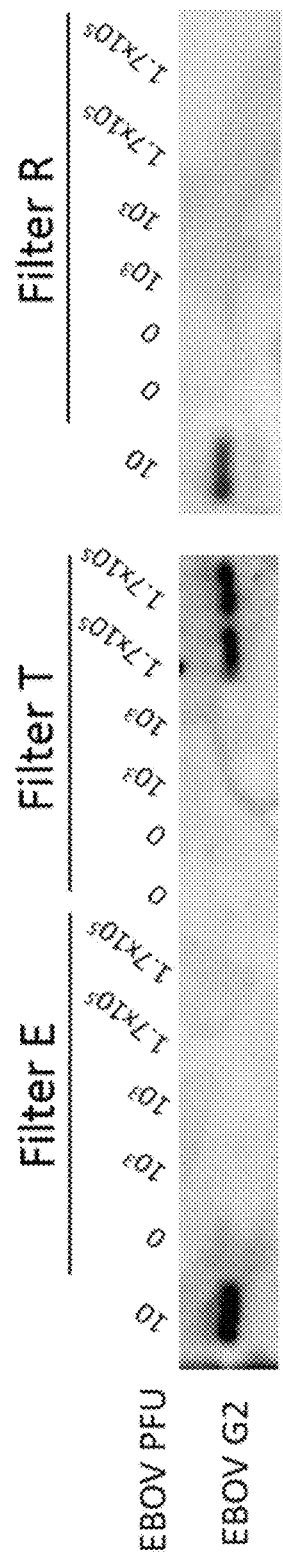
FIG. 5 is an illustration showing detection of EBOV G2 protein by Western Blot following inoculation with filter paper spiked with live Ebola virus.

The same samples evaluated by plaque assay (above in Table 2) were also evaluated by Western Blot to detect the EBOV G2 protein after 14 days infection. The results provided in FIG. 5 confirm those shown in Table 2 showing the detection of EBOV G2 protein from untreated cellulose (T) but not treated cellulose (R, E) by Western Blot. The composition of the filter paper was further described in Table 1.

In order to determine if EBOV RNA is quantitatively detectable from filter paper after extraction of dried blood spots, known amounts of EBOV ($10^5$, $10^4$, $10^3$, and $10^1$ PFU) were spiked into whole mouse blood. Samples (50 μL) were spotted and then dried onto the filter papers for 30 minutes in the BSC and then transferred to ziplock Mylar bags containing desiccant packs for storage at room temperature. After 24 hours, two 7 mm punches were removed and rehydrated for 10 minutes with 15 μL of proteinase K solution (4 mg/ml proteinase K+0.5% SDS). The punches were transferred to a tube containing TRIzol, vortexed, and incubated at room temperature by shaking the tubes at 300 rpm for 60 minutes. An aliquot of the dilution series was not spotted onto filter paper and was added directly to TRIzol for recovery comparison. Total RNA was then extracted and purified according to the manufacturer's recommendations. The amount and quality of viral RNA recovered from the filter papers after 24 hours of dry storage was then evaluated. Samples of each RNA eluate were analyzed using an Agilent bioanalyzer in order to assess the quality of total RNA recovered after 24 hours of dry storage. The Agilent RNA 6000 Pico Kit was followed according to manufacturer's recommendations. Quantitative reverse-transcriptase PCR was used to estimate the number of intact viral genomes present in the filter paper eluate. The assay used was previously published (Weidmann et al., 2004. J. Clinical Virology 30: 94-99), which was designed to detect the nucleoprotein gene of EBOV. EBOV RNA copy number was determined using RNA obtained from BEI Resources (NIAID, NIH: RNA from Zaire Ebolavirus, Mayinga, NR-31806). Percent recovery was calculated by dividing the number of EBOV RNA copies detected in each filter paper eluate by the total number of EBOV RNA copies detected from paired samples (of the same EBOV inoculum) that were not exposed to the filter paper. That ratio was multiplied by 100% to give percent recovery.

Figure 6:
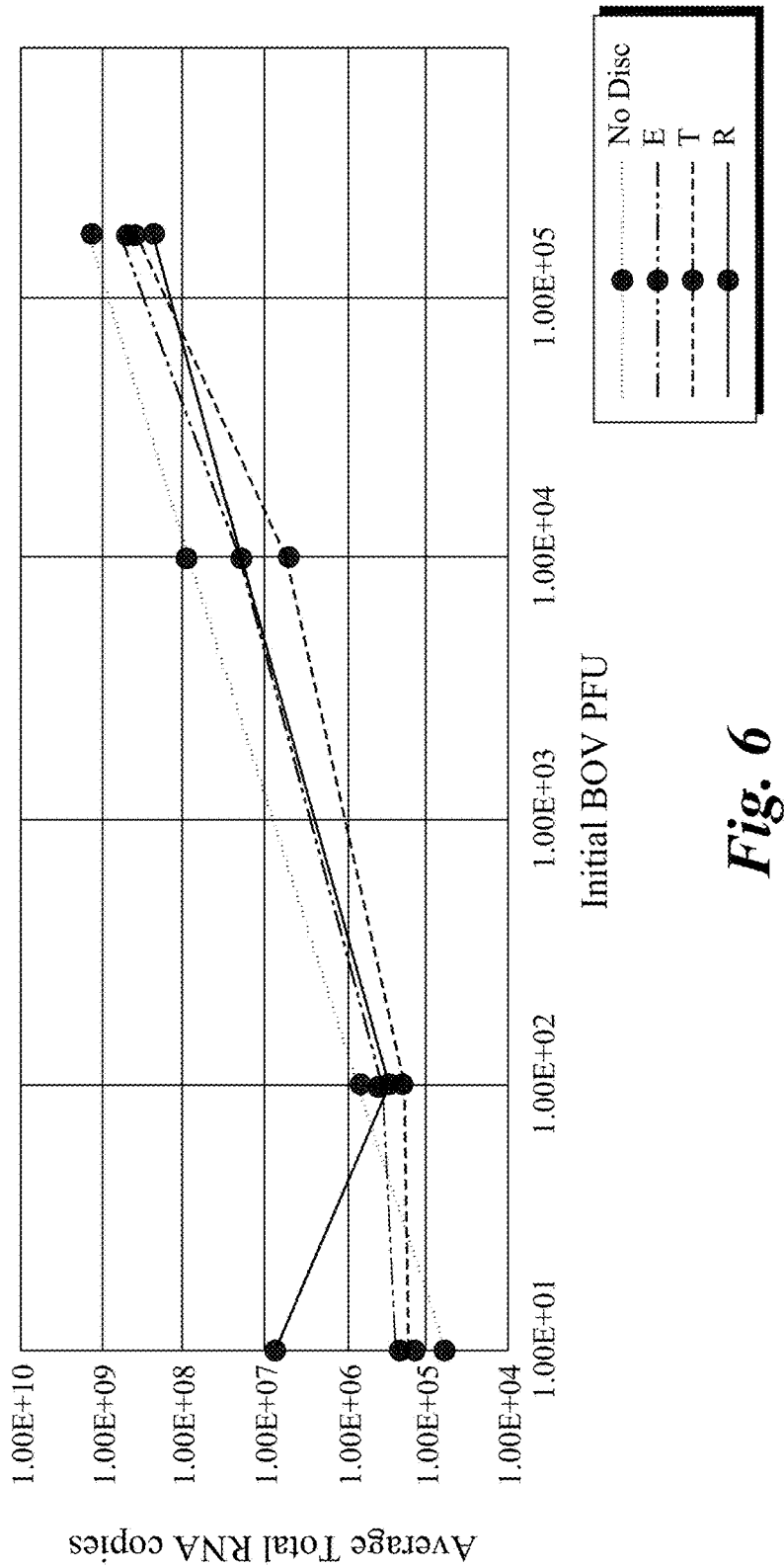
FIG. 6 is a graph showing EBOV PFU versus average total viral RNA copies recovered and detected from dried blood spot eluates by RT-qPCR.
Figure 7:
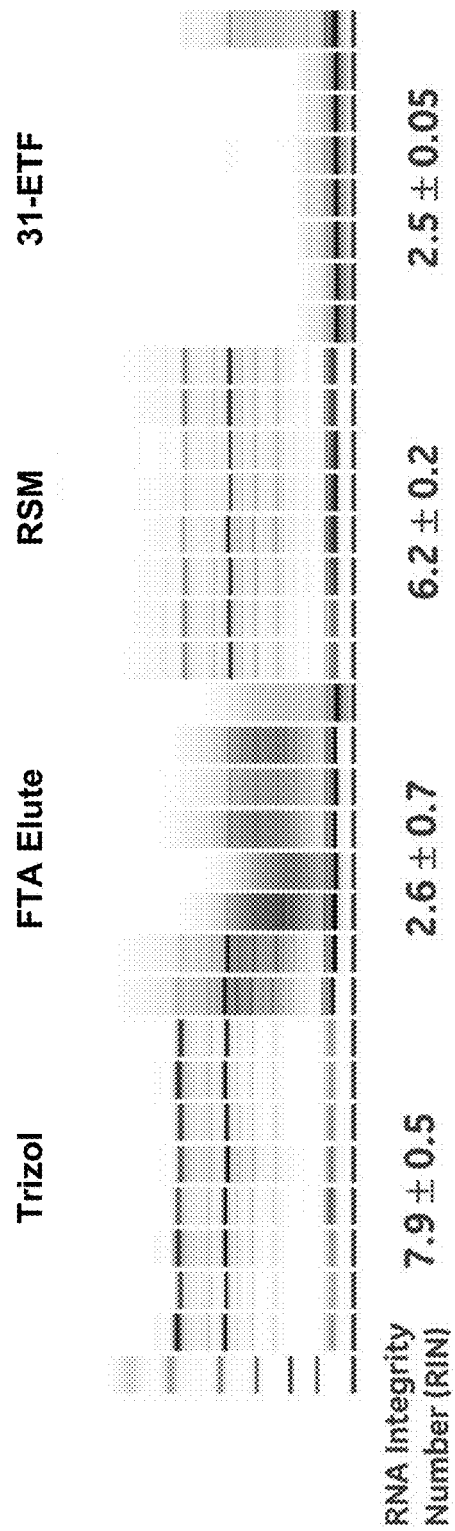
FIG. 7 is an illustration of Agilent Bioanalyzer electrophoretogram data and RNA Integrity Numbers (RIN) for total RNA recovered from dried blood spot eluates after overnight ambient storage compared to Trizol extraction of unstored samples.

FIG. 6 shows the results for one-step RT-qPCR detection of EBOV nucleoprotein gene from extracted dried blood spots as a function of infectious particles (PFU). The EBOV nucleoprotein gene was successfully detected from all dosed filter paper specimens using a ~100 bp amplicon that is relatively insensitive to RNA degradation as a consequence of its small size. However, Bioanalyzer analysis of total RNA revealed that only RSM filter paper (R) successfully preserved RNA integrity (RIN>5) similar to Trizol standard practices (FIG. 7). All together, a comparison of these experiments in Table 3 summarizes Ebola inactivation at the highest tested viral dose and determination of total RNA integrity.

TABLE 3

Comparison of Ebola inactivation and RNA integrity:

| Sample | Ebola inactivated at tested dose ($1.7 \times 10^5$ PFU)? | Total RNA stabilized? | RT-PCR virus detection down to $10^1$ PFU dilution? |
| --- | --- | --- | --- |
| Standard Trizol decontamination | Yes | Yes RIN score = 7.9 ± 0.5 | Yes |
| R | Yes | Yes RIN score = 6.2 ± 0.2 | Yes |
| E | Yes | No RIN score = 2.6 ± 0.7 | Yes |
| T | No | No RIN score = 2.5 ± 0.05 | Yes |

The results in Table 3 demonstrate that RSM filter paper performs similarly to standard Trizol decontamination, but unlike Trizol, enables dry handling and ambient stabilization. Thus, the performance of RSM adheres to CDC guidelines for molecular diagnosis of pathogens, in that a total loss of infectiousness is observed while conserving the integrity of the nucleic acids.

Example 2: Extraction-Free RT-PCR Detection of Ebola from Filter Paper

Ebola-specific primers were ordered from Integrated DNA Technologies (Coralville, Iowa). SEQ ID NO1 and SEQ ID NO2 were purified by desalting. Ebola RNA was obtained through BEI Resources, NIAID, NIH: RNA from Zaire Ebolavirus, Mayinga, NR-31806. This viral stock contained $4.5 \times 10^8$ genomic RNA copies/µl in a background of Vero E6 cellular RNA. Human whole blood stabilized with citrate-phosphate-dextrose solution was spotted onto 31-ETF, FTA Elute, RSM filter papers simultaneously with Ebola RNA (using separately loaded pipettes that were expelled onto the same area of the paper) to a final Ebola genome equivalent of $10^7$-$10^9$ per mL. These Ebola concentrations (RNA copies/mL) simulate the burden of disease approximately 3 days following onset of fever in humans. Spiked blood samples (~25 µL) were allowed to dry on filter paper and were stored overnight at ambient temperature in a desiccator cabinet to simulate delayed processing.

For extraction-free detection of Ebola, a single 1.2 mm punch was obtained from the center of each dry blood spot using a Harris Micro-punch and ejected directly into a 20 µL cDNA synthesis reaction. By volumetric absorption, each punch was estimated to contain approximately 1 µL of the original sample, so the template input range of Ebola RNA was expected to be $10^4$-$10^6$ copies per punch. Consequently, for control purposes, an equivalent input of stock Ebola RNA ($10^4$ or $10^6$ copies) were tested by RT-qPCR alongside filter paper samples. An AffinityScript cDNA Synthesis kit (Agilent Technologies) was used to generate cDNA from each Ebola RNA control and 1.2 mm dried blood spot using random primers. Parallel reactions containing Ebola RNA controls or 1.2 mm dried blood spots but lacking reverse transcriptase enzyme were created to assess background signal from genomic DNA. All cDNA reactions were incubated at 25° C. for 5 minutes, followed by 45 minutes at 42° C. and then inactivated at 95° C. for 5 minutes. The resulting cDNA was then applied to qPCR reactions containing Ebola-specific primers to detect Ebola signal in real-time using an ABI 7500 device (Thermo Fisher Scientific). Briefly, for each sample, 5 µL of cDNA was mixed with 12.5 µL of 2× SensiMix SYBR Master mix (OriGene Technologies), 1 µL of 10 µM primer mix, and 6.5 µL of nuclease-free water to create 25 µL real-time qPCR reactions. These reactions were incubated at 95° C. for 10 minutes, then cycled at 95° C. for 5 seconds and 60° C. for 31 seconds for a total of 40 cycles. SYBR fluorescence was read at each cycle and plotted to calculate the CT threshold at which Ebola was detectable.

Figure 8:
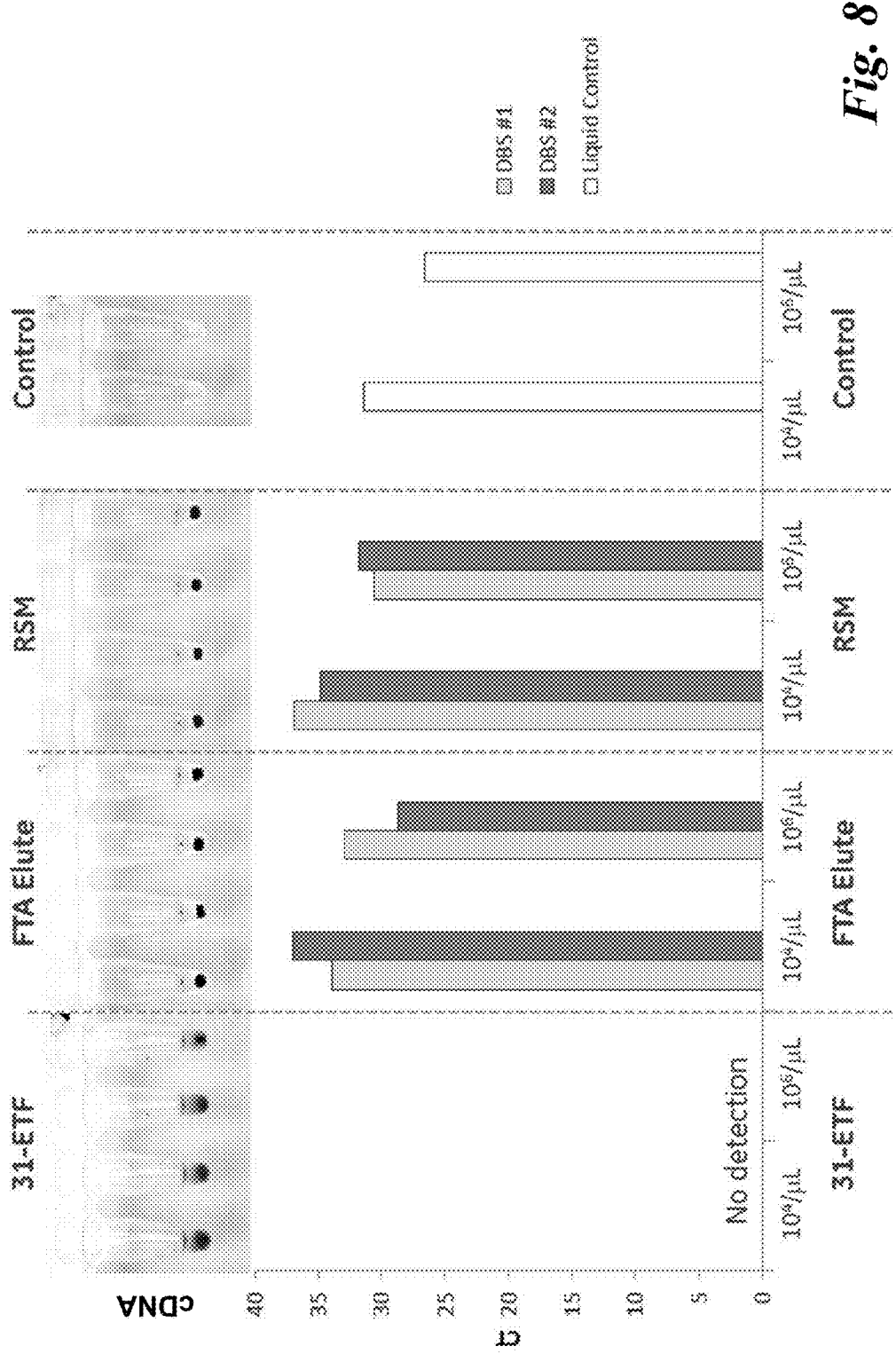
FIG. 8 is a graph illustrating extraction-free RT-qPCR detection of Ebola RNA directly from dried blood spots on filter paper.

FIG. 8 shows the results for two-step RT-qPCR detection of Ebola RNA from different filter paper punches using the extraction-free protocol described above. Ebola RNA was successfully detected directly from dry blood spots on FTA Elute and RSM filter paper across the spiked range ($10^7$-$10^9$ RNA copies per mL). Control reactions verified that these filter paper punches contained approximately $10^4$-$10^6$ RNA copies per microliter. No detection was observed in control reactions lacking reverse transcriptase, demonstrating primer specificity for cDNA rather than genomic DNA. Importantly, detection was not successful from untreated filter paper samples (31-ETF), and in the prior cDNA synthesis step it was noted that blood had leached off 31-ETF filter paper as shown in FIG. 7. In contrast, both FTA Elute and RSM samples retained blood components on the filter paper matrix. Thus, the success of Ebola detection using this extraction-free approach is dictated by how well the filter paper collection matrix retains blood inhibitors during punch-in cDNA synthesis and subsequent downstream qPCR detection steps.

Example 3: Extraction-Free Isothermal Amplification and Detection of Ebola from Filter Paper Ebola-specific primers were ordered from Integrated DNA Technologies (Coralville, Iowa). SEQ ID NO3 and SEQ ID NO4 were purified by desalting, while SEQ ID NO5 and SEQ ID NO6 were purified by HPLC. The recognition site for the nicking endonuclease Nt.BbvCI (New England Biolabs, Inc.) is underlined and the nick site is noted with a caret.

SEQ ID NO1: 5'-d[TCT GAC ATG GAT TAC CAC AAG ATC]-3'

SEQ ID NO2: 5'-d[GGA TGA CTC TTT GCC GAA CAA TC]-3'

-continued

SEQ ID NO3: 5'-d[GTC CTC AGA AAA TCT GGA T]-3'

SEQ ID NO4: 5'-d[TTC AAG ATT GTT TAC TTG ATA CAC]-3'

SEQ ID NO5: 5'-d[GCA TAA TAC TAC CAG TCT CCT ^ CAG CTC TGA CAT GGA TTA CCA C]-3'

SEQ ID NO6: 5'-d[GCA TAA TAC TAC CAG TCT CCT ^ CAG CTG ACT CTT TGC CGA AC]-3'

The following reagent was obtained through BEI Resources, NIAID, RNA from Zaire Ebolavirus, Mayinga, NR-31806. This viral stock contained 4.5E+08 genomic RNA copies/μl in a background of Vero E6 cellular RNA and was diluted 1:10,000 (now 45,000 Ebola genomic equivalents/μl) in RNase-free TET Buffer (10 mM Tris, pH 8 (Sigma Aldrich) containing 0.1 mM EDTA (Life Technologies) and 0.01% Tween 20 (Sigma Aldrich)). The diluted RNA was stored in 100 μl aliquots at −80° C. Primers for Zaire Ebolavirus, Mayinga RNA (SEQ ID NO 1-4) were designed from the published sequence (GenBank: AY142960).

A 10 μl combined isothermal reverse transcription/amplification reaction (RT-iSDA) contained the following components: 50 nM Seq ID NO3, 50 nM SEQ ID NO4, 0.5 μM SEQ ID NO5, 0.25 μM Seq ID NO6, 200 μM dATP (GE Healthcare), 200 μM dCTP (GE Healthcare), 200 μM dGTP (GE Healthcare), 200 μM dTTP (GE Healthcare), 50 mM Tris-HCl, pH 7.4 (Sigma Aldrich), 5 mM magnesium sulphate (New England Biolabs, Inc.), 40 mM potassium phosphate buffer, pH 7.4 (J. T. Baker), 10 units RNase Inhibitor (Life Technologies), 2 units Omniscript™ Reverse Transcriptase (Qiagen), 8 units Bst WarmStart® DNA Polymerase (New England Biolabs, Inc.) and 3.2 units Nt.BbvCI (New England Biolabs, Inc.). Increased volume reactions, e.g., 50 μl or 75 μl, were scaled proportionally. Ebola RNA template was added either in solution at the indicated copy number or as part of/in conjunction with a 1.2 mm punch (Harris MICRO-PUNCH®) of RNA Stabilization Matrix (RSM). All reactions were incubated at 50° C. for 20 minutes and an aliquot from each analyzed by electrophoresis at 70° C. through a 15% TBE-Urea gel (Life Technologies). Just prior to electrophoresis, 2 μl from a reaction were mixed with 6 μl of Gel Loading Buffer II (Life Technologies), denatured at 95° C. for 2 minutes and immediately quenched on ice. Five microliters from each denatured sample were immediately loaded in a well of the gel. Gels were stained for 15 minutes after electrophoresis in a 2× solution of SYBR® Green II (Life technologies), diluted according to the manufacturer's instructions, and then visualized using a Typhoon™ FLA 9500 (GE Healthcare) variable mode laser scanner.

Human blood was obtained from GE Medical Services (Niskayuna, N.Y.) using approved IRB protocol #13095. RSM containing human blood and viral RNA was prepared by having 8 μl of blood in one pipette tip and 8 μl of Zaire Ebolavirus RNA at 45,000 copies/μl in another pipette tip and concurrently expelling them in the same area of the paper. Blood and RNA were mixed so that the center of the spot was about 0.7 cm from the edge of the paper. The spot was allowed to air dry and the paper stored desiccated at room temperature. After drying, some RSM samples were cut into strips so that the blood RNA spot was at the bottom, and strips were washed by lateral flow using TET Buffer and a wick of CF7 paper (GE Healthcare). Once washed, strips were allowed to air dry before use and a 1.2 mm punch was used for isothermal amplification. In other cases, RSM samples were not washed by lateral flow but rather a 1.2 mm punch from the dried blood spot was ejected directly into a 75 μL isothermal amplification reaction.

FIGS. 9A through 9C demonstrate combined isothermal reverse transcription/amplification from RSM with or without washing a 1.2 mm punch prior to the reactions. The arrows indicate the expected reverse transcribed amplification products (a fully-nicked 81 base amplicon and a partially nicked 102 base amplicon). FIG. 9A shows control reactions A, B and C were each reaction had volumes of 50 μl. Reaction A did not contain template, while B and C each contained 45,000 copies of Zaire Ebolavirus RNA. Reaction D additionally contained 0.5 μl of whole human blood. FIG. 9B shows control reactions E and F were each reaction volumes of 10 μl. Reaction E did not contain template while F contained 45,000 copies of Zaire Ebolavirus RNA. FIG. 9C shows reactions G and H were each reaction volumes of 10 μl containing a 1.2 mm punch of washed RSM that had previously been spotted with human blood and Ebola RNA. Reaction H had extra 45,000 copies of Zaire Ebolavirus RNA added separately to the reaction in addition to the washed punch of RSM. Reaction I was a 75-μl reaction volume containing an unwashed 1.2 mm punch of RSM that was spotted with human blood and 45,000 copies of Ebola RNA. No blood components were observed to leach from RSM filter paper during isothermal amplification.

The invention claimed is:

1. A method of inactivation and dry storage of a biological sample containing an RNA virus, the method comprising:
providing a non-dissolvable, dry, solid matrix incorporated with a composition, the composition comprising at least one protein denaturant, at least one acid or acid-titrated buffer reagent impregnated therein in a dry state to provide an acidic pH on hydration;
contacting the biological sample with the non-dissolvable, dry, solid matrix to effectively lyse cells of the biological sample to extract RNA from the lysed cells and preserve the extracted RNA in an intact state;
drying the biological sample on the solid matrix; and
storing the biological sample on the solid matrix in a dry state under ambient conditions,
wherein the biological sample is rendered non-infectious within 30 minutes of being subjected to the drying step, and wherein the acidic pH is in a range from 2 to 7.

2. The method of claim 1, wherein the acid comprises acetic acid, citric acid, tartaric acid, phosphoric acid, hydrochloric acid, Tris(2-carboxyethyl) phosphine-hydrochloric acid (TCEP-HCl), oxidized Tris(2-carboxyethyl) phosphine-hydrochloric acid (TCEP-O-HCl), sulfuric acid, nitric acid, vanillic acid, 3-(N-morpholino)propanesulfonic acid or combinations thereof.

3. The method of claim 1, wherein the composition further comprises a UV protectant, a free-radical scavenger, a chelator, a reducing agent or combinations thereof.

4. The method of claim 1, wherein the composition further comprises an RNase inhibitor.

5. The method of claim 4, wherein the RNase inhibitor comprises at least one of a triphosphate salt, pyrophosphate salt, vanadyl ribonucleoside complex (VCR), or sodium pyrophosphate.

6. The method of claim 3, wherein the reducing agent is selected from the group consisting of dithiothreitol (DTT), 2-mercaptoethanol (2-ME), tris(2-carboxyethyl)phosphine (TCEP), tris(2-carboxyethyl)phosphine hydrochloride (TCEP-HCl), and combinations thereof.

7. The method of claim 1, wherein the extracted and preserved RNA has an RNA integrity number (RIN) of greater than 5.

8. The method of claim 1, wherein the RNA virus is a blood-borne virus.

9. The method of claim 8, wherein the blood-borne virus is Ebolavirus, Hepatitis virus, Arenavirus, Filovirus, Lentivirus, or a related subgroup.

10. The method of claim 1, wherein the method further comprises recovering the RNA from the non-dissolvable, dry, solid matrix.

11. The method of claim 10, wherein recovering the RNA comprises extracting the RNA by rehydrating the non-dissolvable, dry, solid matrix, solid phase extraction, electroelution, or combinations thereof.

12. The method of claim 11, wherein rehydrating comprises using an aqueous solution, a buffer solution, an organic solution, or combinations thereof.

13. A method for testing a biological sample for presence of an RNA virus, the method comprising:
providing a non-dissolvable, dry, solid matrix incorporated with a composition, the composition comprising at least one protein denaturant, at least one acid or acid-titrated buffer reagent impregnated therein in a dry state to provide an acidic pH on hydration;
applying the biological sample comprising RNA to the non-dissolvable, dry, solid matrix;
drying the biological sample on the non-dissolvable, dry, solid matrix to preserve the RNA in an intact state;
recovering the RNA of the biological sample from the non-dissolvable, dry, solid matrix; and
analyzing the recovered RNA for the presence of a viral RNA to determine the presence of the RNA virus, wherein the biological sample is rendered non-infectious within 30 minutes of being subjected to the drying step, and wherein the acidic pH is in a range from 2 to 7.

14. The method of claim 13, wherein the recovering step comprises extracting the RNA by rehydrating the non-dissolvable, dry, solid matrix, electroelution, solid phase extraction, adding a portion of the solid matrix directly into an amplification reaction, or combinations thereof.

15. The method of claim 14, wherein rehydrating comprises using an aqueous solution, a buffer solution, an organic solution, or combinations thereof.

16. The method of claim 13, wherein the acid comprises acetic acid, citric acid, tartaric acid, phosphoric acid, hydrochloric acid, Tris(2-carboxyethyl) phosphine-hydrochloric acid (TCEP-HCl), oxidized Tris(2-carboxyethyl) phosphine-hydrochloric acid (TCEP-O-HCl), sulfuric acid, nitric acid, vanillic acid, 3-(N-morpholino)propanesulfonic acid, or combinations thereof.

17. The method of claim 13, wherein the composition further comprises a UV protectant, a free-radical scavenger, a chelator, a reducing agent or combinations thereof.

18. The method of claim 13, wherein the composition further comprises an RNase inhibitor.

19. The method of claim 18, wherein the RNase inhibitor comprises at least one of a triphosphate salt, pyrophosphate salt, vanadyl ribonucleoside complex (VCR), or sodium pyrophosphate.

20. The method of claim 17, wherein the reducing agent is selected from the group consisting of dithiothreitol (DTT), 2-mercaptoethanol (2-ME), tris(2-carboxyethyl)phosphine (TCEP), tris(2-carboxyethyl)phosphine hydrochloride (TCEP-HCl) and combinations thereof.

21. The method of claim 13, wherein the biological sample is blood.

22. The method of claim 13, wherein the RNA virus is a blood-borne virus.

23. The method of claim 22, wherein the blood-borne virus is Ebolavirus, Hepatitis virus, Arenavirus, Filovirus, Lentivirus, or a related subgroup.

24. The method of claim 13, further comprising prolonged storing the RNA in an intact form under a dry format and ambient conditions, wherein any virus present in the biological sample is rendered inactive.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tctgacatgg attaccacaa gatc                                              24

<210> SEQ ID NO 2
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
ggatgactct ttgccgaaca atc                                           23

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtcctcagaa aatctggat                                                19

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcaagattg tttacttgat acac                                          24

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcataatact accagtctcc tcagctctga catggattac cac                     43

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcataatact accagtctcc tcagctgact ctttgccgaa c                       41
```